(12) United States Patent
Kaess et al.

(10) Patent No.: US 8,776,598 B2
(45) Date of Patent: Jul. 15, 2014

(54) LIQUID SENSOR

(75) Inventors: Udo Kaess, Stuttgart (DE); Volker Haller, Holzgerlingen (DE); Monika Scherer, Giessem (DE); Gustav Klett, Moessingen (DE); Markus Niemann, Beckingen (DE)

(73) Assignee: Robert Bosch GmbH, Stuttgart (DE)

( * ) Notice: Subject to any disclaimer, the term of this patent is extended or adjusted under 35 U.S.C. 154(b) by 1190 days.

(21) Appl. No.: 12/672,655

(22) PCT Filed: Jul. 2, 2008

(86) PCT No.: PCT/EP2008/058482
§ 371 (c)(1),
(2), (4) Date: Jul. 8, 2011

(87) PCT Pub. No.: WO2009/019084
PCT Pub. Date: Feb. 12, 2009

(65) Prior Publication Data
US 2011/0308304 A1    Dec. 22, 2011

(30) Foreign Application Priority Data
Aug. 8, 2007 (DE) .......................... 10 2007 037 364

(51) Int. Cl.
*G12B 9/06* (2006.01)
(52) U.S. Cl.
CPC ........................................ *G12B 9/06* (2013.01)
USPC ........ 73/431; 73/290 R; 73/304 R; 73/304 C; 73/866.5
(58) Field of Classification Search
USPC .............. 73/290 R, 304 R, 304 C, 431, 866.5
See application file for complete search history.

(56) References Cited

U.S. PATENT DOCUMENTS

| 2,582,400 | A | * | 1/1952 | Smith | 73/304 C |
| 2,904,751 | A | * | 9/1959 | Parsons | 324/663 |
| 3,433,072 | A | * | 3/1969 | Auer et al. | 73/304 R |
| 3,831,069 | A | * | 8/1974 | Merrell et al. | 361/272 |
| 3,861,559 | A | * | 1/1975 | McCormick | 220/664 |
| 3,901,079 | A | * | 8/1975 | Vogel | 73/304 C |
| 3,988,668 | A | * | 10/1976 | Bowers | 324/690 |
| 4,296,472 | A | * | 10/1981 | Sarkis | 702/52 |
| 4,428,232 | A | * | 1/1984 | Tanaka et al. | 73/304 C |
| 4,574,328 | A | * | 3/1986 | Maier | 361/284 |
| 4,662,232 | A | * | 5/1987 | Gonsalves et al. | 73/866.5 |
| 4,806,847 | A | * | 2/1989 | Atherton et al. | 73/304 C |

(Continued)

FOREIGN PATENT DOCUMENTS

| DE | 197 57 924 | 7/1999 | |
| EP | 40888 A1 * | 12/1981 | G01F 23/26 |

(Continued)

OTHER PUBLICATIONS

International Search Report for PCT/EP2008/058482, dated Sep. 11, 2008.

*Primary Examiner* — David A Rogers
(74) *Attorney, Agent, or Firm* — Kenyon & Kenyon LLP

(57) ABSTRACT

A fluid sensor includes a metal housing body, which has a box and a flanged ring circumferentially surrounding the box. A housing jacket is formed from plastic material and disposed on an exterior side of the housing body. A sealing ring, which is situated circumferentially on top of the flanged ring, subdivides the housing jacket into two sections that are insulated from each other.

9 Claims, 6 Drawing Sheets

(56) References Cited

U.S. PATENT DOCUMENTS

Figure 1:
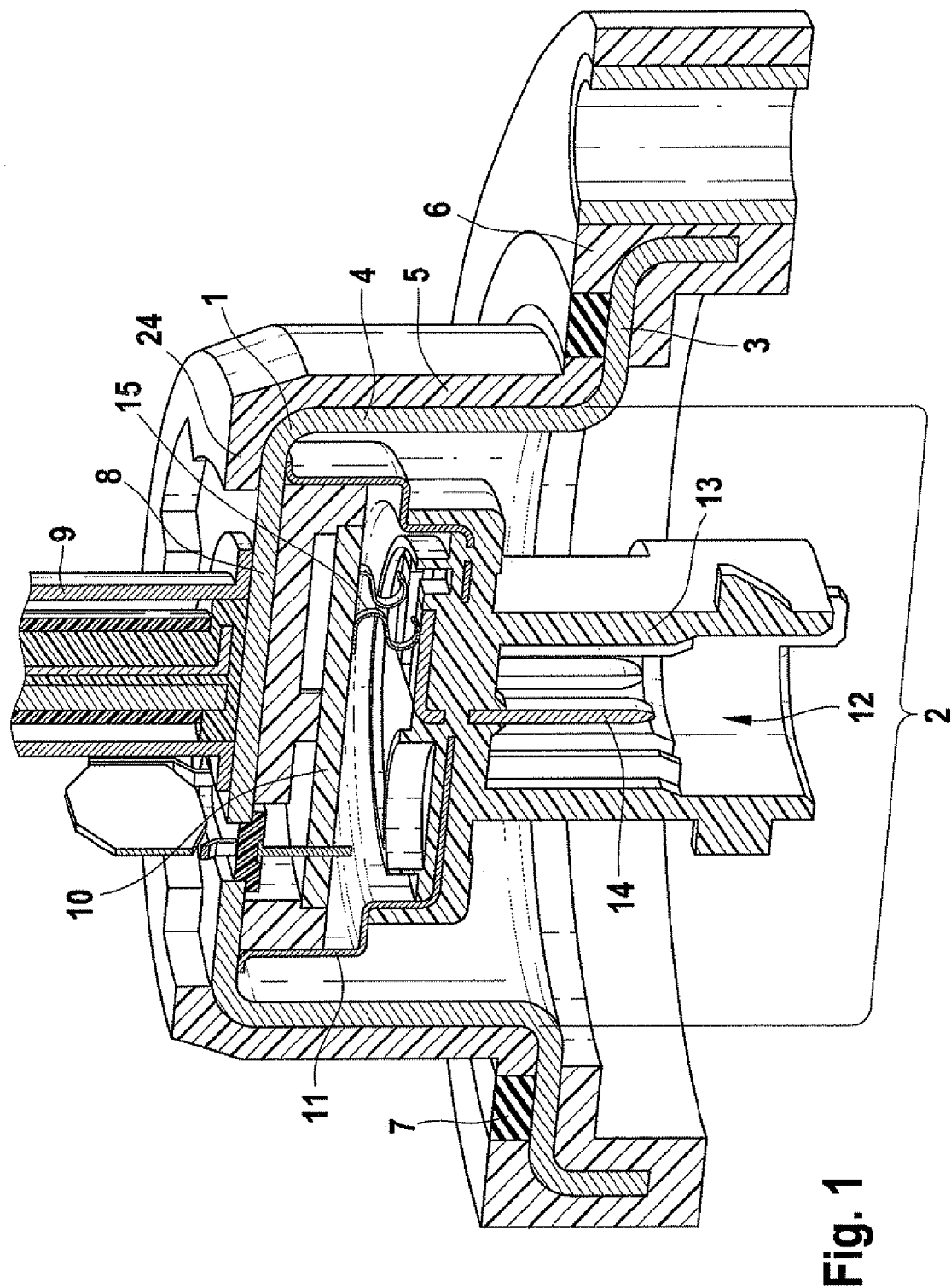

| | | | |
|---|---|---|---|
| 4,845,986 A * | 7/1989 | Hayashi et al. | 73/290 R |
| 5,481,197 A * | 1/1996 | Sanders et al. | 324/690 |
| 5,753,835 A * | 5/1998 | Gustin | 73/866.5 |
| 5,907,278 A * | 5/1999 | Park et al. | 340/450.3 |
| 5,929,754 A * | 7/1999 | Park et al. | 340/439 |
| 6,019,007 A * | 2/2000 | Grieger et al. | 73/866.5 |
| 6,029,514 A * | 2/2000 | Adam et al. | 73/149 |
| 6,380,750 B1 * | 4/2002 | Schenck et al. | 324/690 |
| 6,443,756 B1 * | 9/2002 | Hagmann et al. | 439/402 |
| 6,935,173 B2 * | 8/2005 | Stehman et al. | 73/304 C |
| 7,329,338 B2 * | 2/2008 | Sieth et al. | 210/96.1 |
| 7,373,818 B2 * | 5/2008 | Schmidt et al. | 73/304 R |
| 7,698,940 B2 * | 4/2010 | Osswald et al. | 73/304 C |
| 7,766,547 B2 * | 8/2010 | Weppenaar et al. | 374/208 |
| 7,963,164 B2 * | 6/2011 | Ross et al. | 73/304 C |
| 2004/0093943 A1 * | 5/2004 | Arias | 73/304 C |
| 2006/0123933 A1 * | 6/2006 | Braaten | 73/866.5 |
| 2006/0196263 A1 * | 9/2006 | Stahlmann et al. | 73/304 R |
| 2006/0230827 A1 * | 10/2006 | Klees et al. | 73/304 R |
| 2007/0084281 A1 * | 4/2007 | Fredriksson | 73/290 R |
| 2007/0227276 A1 * | 10/2007 | Jagiella et al. | 73/866.5 |
| 2008/0307882 A1 * | 12/2008 | Schroter et al. | 73/304 |
| 2011/0110794 A1 * | 5/2011 | Mayleben et al. | 417/53 |

FOREIGN PATENT DOCUMENTS

| | | | | |
|---|---|---|---|---|
| FR | 2548361 A1 * | 1/1985 | | G01F 23/26 |
| JP | 2000-507704 | 6/2000 | | |
| JP | 2006-77674 | 3/2006 | | |
| WO | WO 99/28149 | 6/1999 | | |
| WO | WO 2006/067625 | 6/2006 | | |
| WO | WO 2006/133702 | 12/2006 | | |

* cited by examiner

LIQUID SENSOR

CROSS-REFERENCE TO RELATED APPLICATIONS

This application claims benefit to and is a national stage entry of PCT/EP2008/058482 filed on 2 Jul. 2008, which claims benefit to German patent application 10 2007 037 364.5 filed on 8 Aug. 2007.

FIELD OF THE INVENTION

The present invention relates to a liquid sensor, in particular a liquid-level sensor for fuel, and/or a liquid sensor for an engine oil composition.

BACKGROUND INFORMATION

A liquid-level sensor is known from DE 197 57 924 A1. Two tubular electrodes disposed inside one another are used to determine the dielectric constant or the specific resistance value of oil. The electrodes are contacted by spring elements.

An additional sensor array for determining the resistance value of oil is described in DE 195 11 556 C1. Two cylindrical electrodes are disposed coaxially and insulated from one another by spacer elements, The liquid-level sensor has a mounting flange on a housing edge.

The housing of the liquid-level sensors is made of plastic. To this end the capacitive measuring elements are extrusion-coated using an appropriate plastic. The affixation in a cavity or in a duct to a cavity may be implemented with the aid of a flange. Sealing is typically accomplished by an adhesive agent.

SUMMARY

The liquid-level sensor having the features described herein has improved mechanical properties.

The liquid sensor according to example embodiments of the present invention includes a metal housing body, which has a box and a flanged ring surrounding the box. A housing jacket is formed from plastic material and disposed on an exterior side of the housing body. A sealing ring, which is situated circumferentially on top of the flanged ring, subdivides the housing jacket into two sections that are insulated from one another. Among other things, the metal housing body provides high mechanical stability of the liquid sensor. For example, the housing jacket reduces the effect of aggressive fluids such as oil on the metal housing body. The sealing ring, given its special placement, ensures that an installed liquid sensor insulatingly seals in fashion a duct inside which it is installed in insulating fashion.

In example embodiments, the sealing ring contacts the metal housing body in the region of the flanged ring.

According to example embodiments, a cylindrical capacitive sensor is welded to an exterior side of the box. Because of the material connection, high mechanical stability of the elongated and projecting capacitive sensor is obtained.

In example embodiments, an insert is inserted into the box, and electronic subassemblies for controlling and/or supplying the liquid sensor are situated on the insert. The insert may be welded to the box.

In example embodiments, a plug connection is affixed on the insert, and conductive elements for the electric contacting of the plug connection are provided on the electronic subassemblies.

The box may have an external thread on its exterior side for mounting the liquid sensor.

Socket connectors for fixing the housing in place may be situated in a first section of the two mutually insulated sections of the housing jacket. A second section of the mutually insulated sections of the housing jacket may cover at least the side walls of the box partially.

The liquid sensor is able to be used as liquid-level sensor for fuel and/or as liquid sensor for an engine-oil composition.

BRIEF DESCRIPTIONS OF THE DRAWINGS

Figure 2:
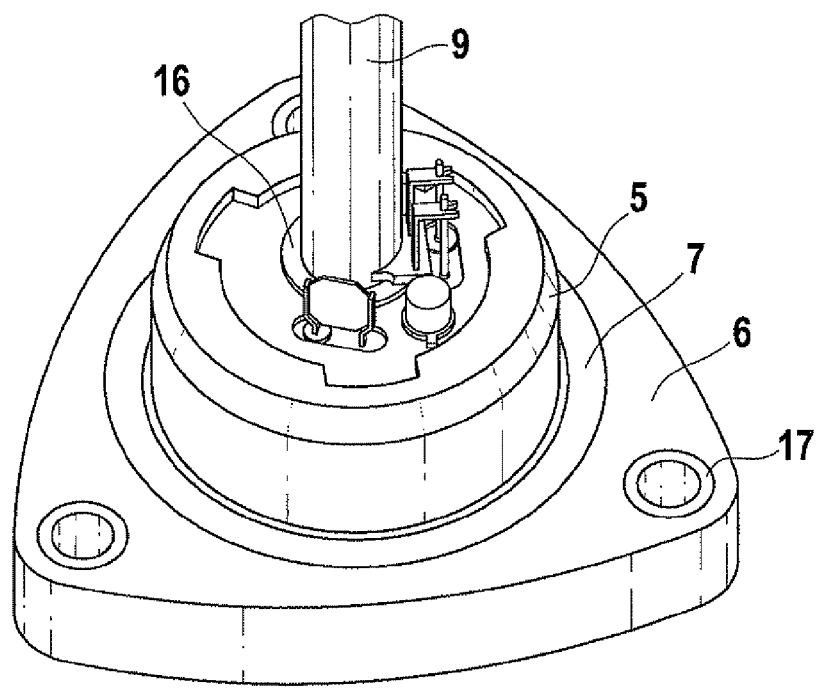
Figure 3:
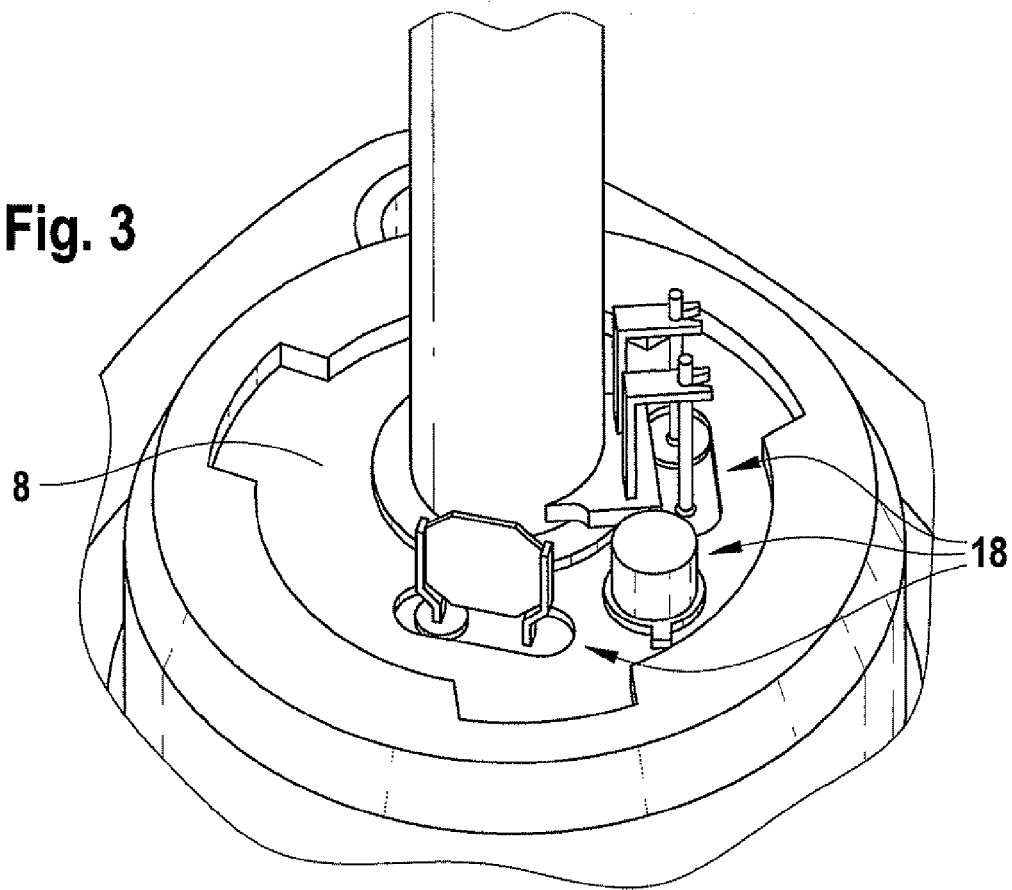
Figure 4:
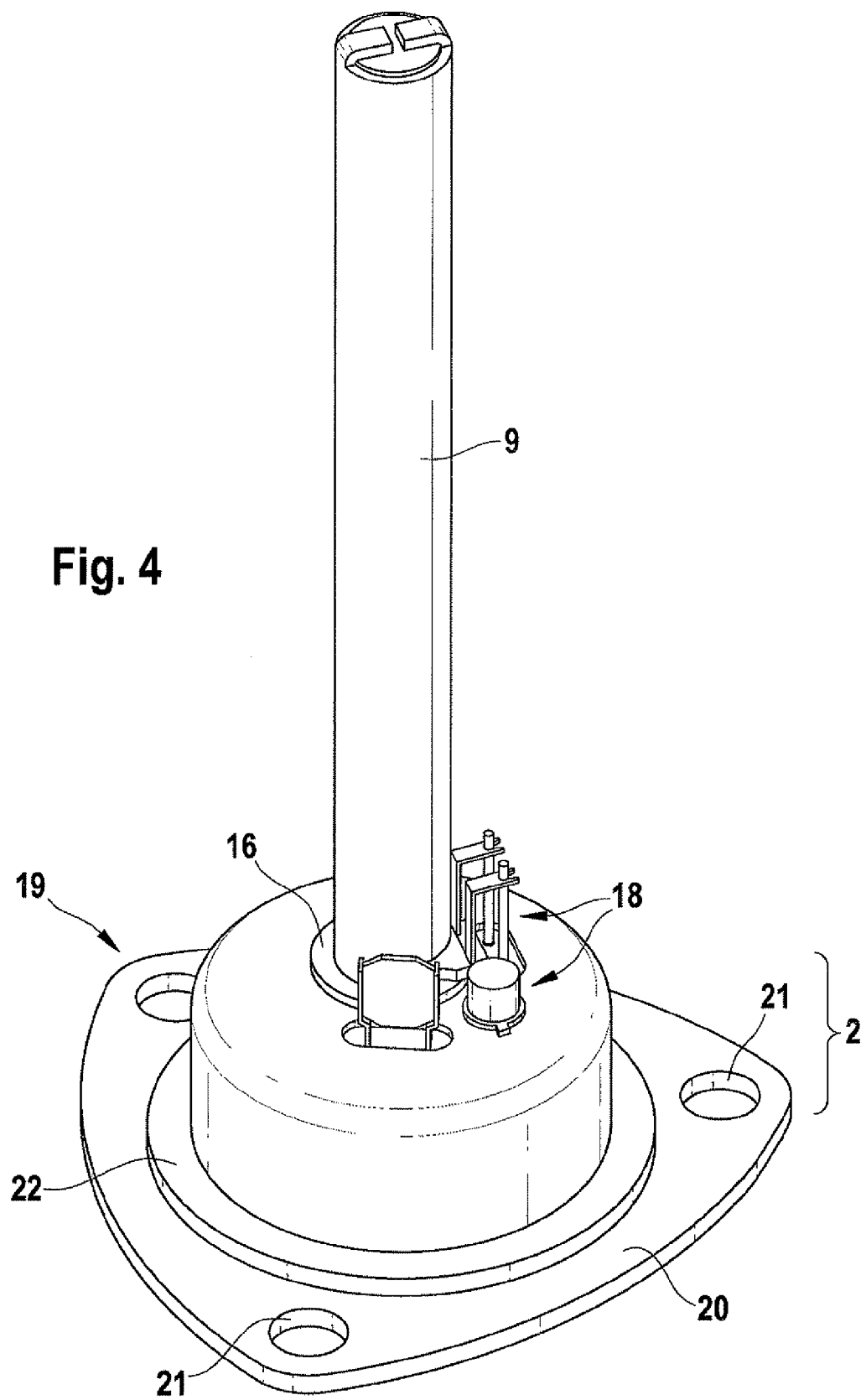
Figure 5:
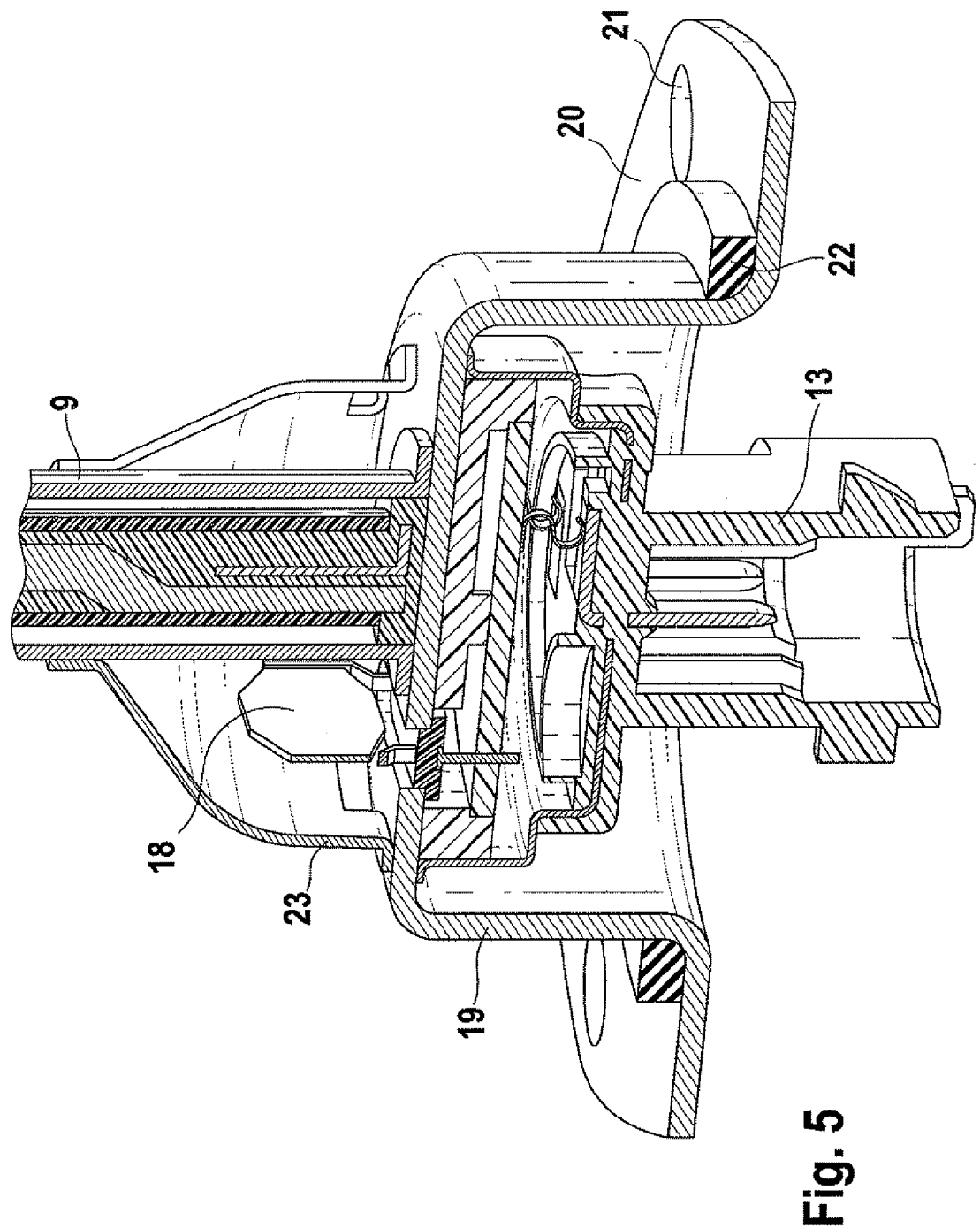
Figure 6:
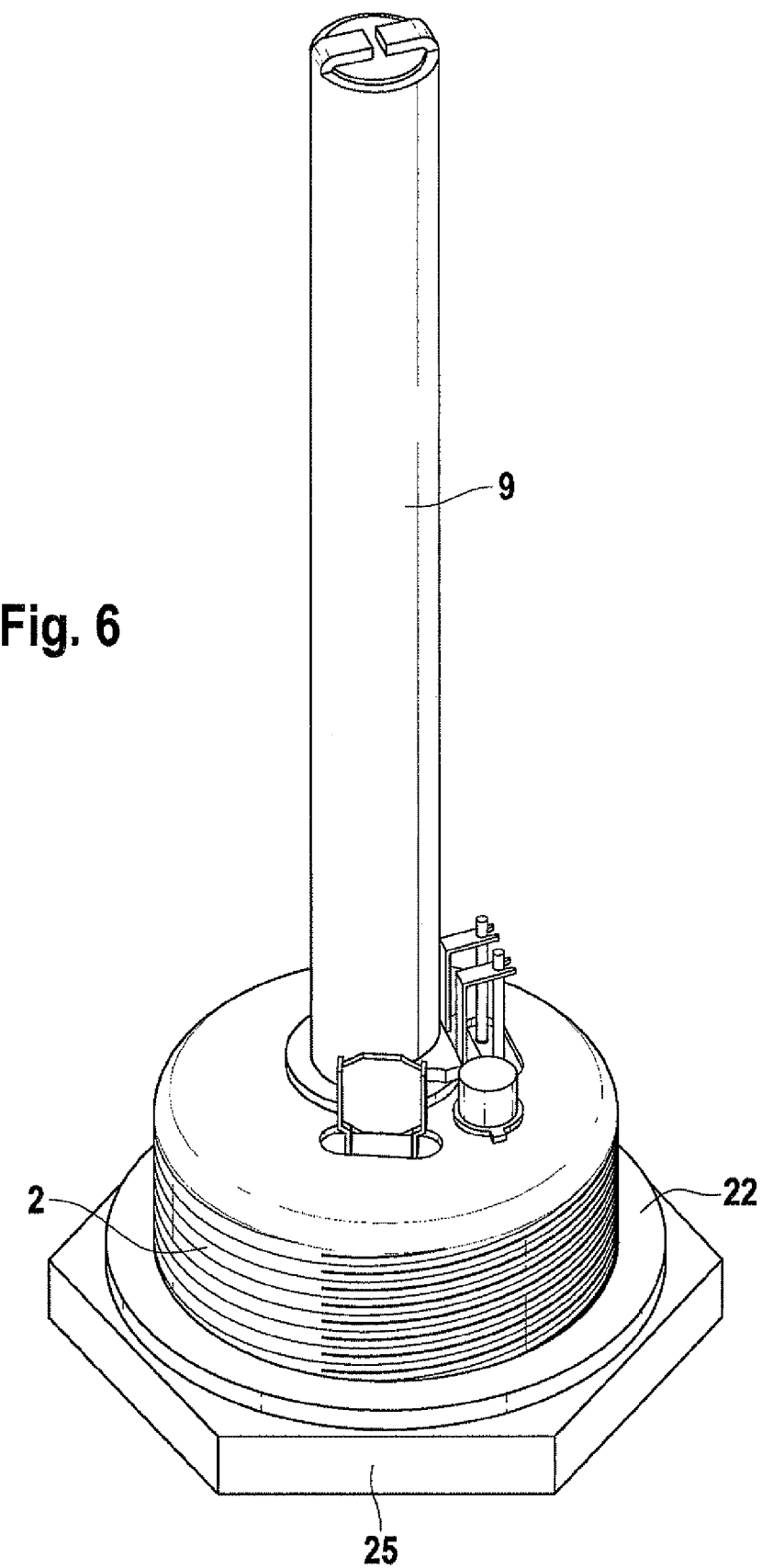
Figure 7:
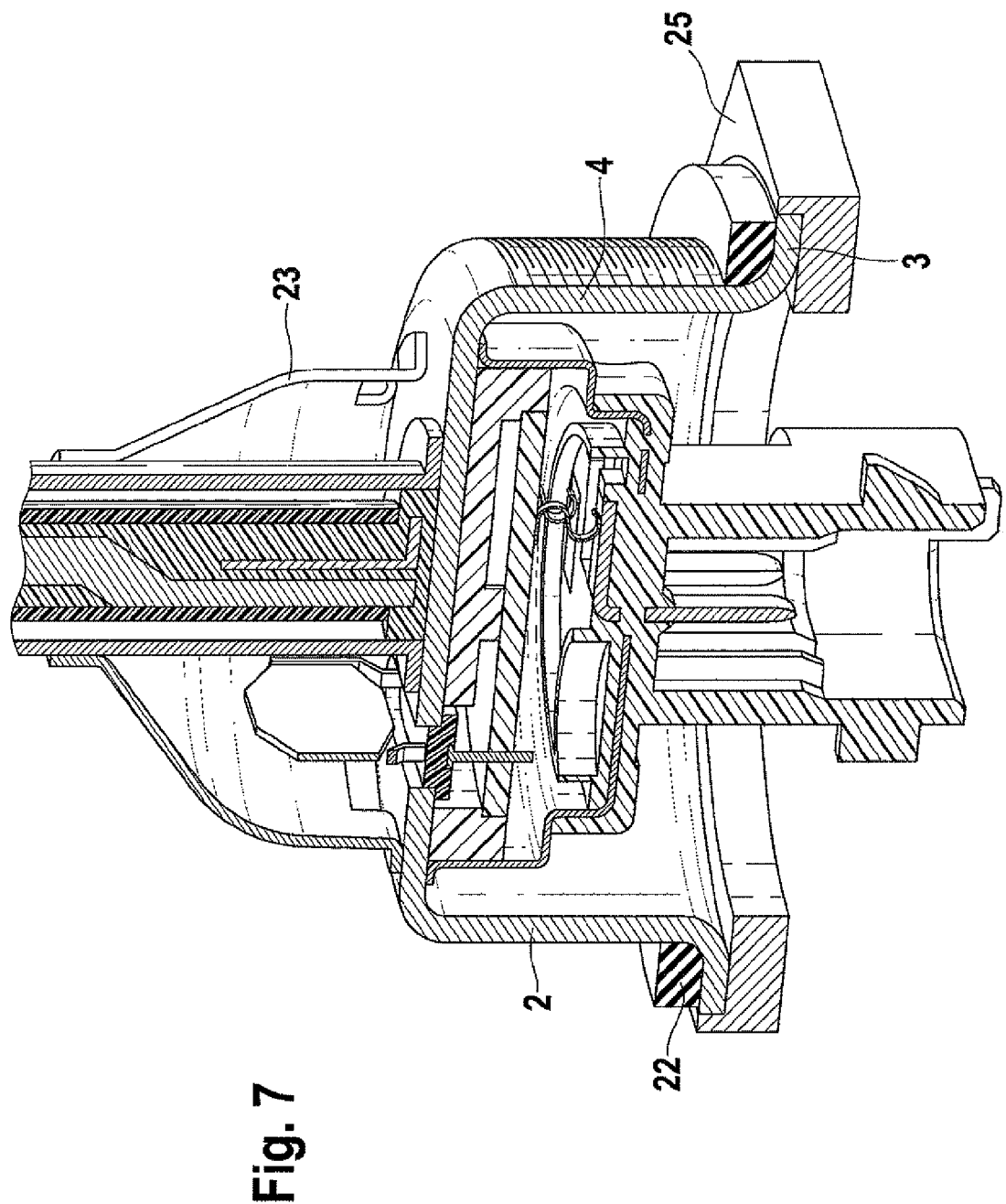

FIG. 1 is a partial cross-section of a liquid sensor;
FIG. 2 is an oblique view of the liquid sensor from FIG. 1;
FIG. 3 is a detail view from FIG. 2;
FIG. 4 is an oblique view of one development of a liquid sensor;
FIG. 5 is a partial cross-section of the liquid sensor from FIG. 4;
FIG. 6 illustrates an additional example embodiment of a liquid sensor; and
FIG. 7 is a partial cross-section of the liquid sensor from FIG. 6.

DETAILED DESCRIPTION

In the figures, identical reference symbols denote identical or similar elements.

A first development will be explained with the aid of FIGS. 1-3 by way of example for a liquid sensor.

A housing of the liquid sensor has a metal housing body 1. Housing body 1 may have the form illustrated in FIG. 1. The form of the housing body includes a box 2, which defines an interior space of the housing. A flanged ring 3 extends at an angle with respect to a wall of box 2. The housing body may be produced by a deep-drawing process, for example. Materials for housing body 1 are iron, steel, stainless steel, aluminum or other metal materials.

In this example embodiment, housing body 1 is largely covered by a two-part housing jacket 5, 6 on its outside. The housing jacket is preferably made from plastic material. The plastic material should be resistant to liquids wetting the liquid sensor. Furthermore, the plastic must have sufficient temperature stability, such as in the range between −40° C. and 150° C., for example.

A first part 5 of the housing jacket covers side walls 4 of box 2. Moreover, an edge region 7 of the base of box 2 may be insulated from the environment by the housing jacket.

A second part of the housing jacket is affixed or mounted on flanged ring 3. Second part 6 may enclose both the upper and the lower side of flanged ring 3.

A sealing material 7 is disposed on flanged ring 3. Sealing material 7 is in direct contact with flanged ring 3. Furthermore, sealing material 7 separates first part 5 from second part 6 of the housing jacket to form two separate components that are not interconnected. Sealing material 7 is built up on flanged ring 3 in completely circumferential fashion. Flanged ring 7 produced in this manner is preferably made from an oil-resistant and elastic material. Among other materials, silicone is suitable for this purpose.

Welded to bottom 8 of box 2 is a capacitive sensor 9. Capacitive sensor 9 may consist of, for example, two cylindrical electrodes disposed inside one another.

A circuit board 10 carrying subassemblies is disposed in the interior of box 2.

The subassemblies include the necessary electronic circuits for operating, controlling, supplying etc. the liquid sensor. An electric connection from the circuit board to capacitive sensor 9 is implemented by ducts through bottom 8. The ducts preferably have a wall made of glass or ceramic to provide electric insulation.

The circuit board may be affixed on housing body 1.

In addition, an insert 11 is disposed inside box 2. Insert 11 together with box 2 forms an enclosed space in which circuit board 10 is situated. To this end, insert 11 is connected to bottom 8 or side wall 4 of box 2 by a continuous welded seam. The welded seam preferably is an airtight seam. This makes it possible to protect the electronic components and circuit board 10 from spray water, corrosive gases etc.

A plug assembly 12 having a plug housing 13 and a blade contact 14 is mechanically connected with insert 11. A plastic layer may be sputtered onto the connection region of plug assembly 12 with insert 11. Plug assembly 12 and insert 11 are preferably injection-molded in sealing fashion. This ensures that the cavity formed by box 2 and insert 11 is airtight, at least impervious to spray water, in the region of the plug assembly as well. Additional sealing using bonding agents is also conceivable. An electrically conductive connection between blade contacts 14 and circuit board 10 may be obtained by spring elements 15. Spring elements 15 may be fixed in place on circuit board 10.

A subassembly, made up of insert 11 and plug assembly 12, may be placed inside the box during the assembly process and then be fixed in place on bottom 8 by welding.

In the oblique view of FIG. 2, a mounting washer 16 of capacitive sensor 9 can be seen. The mounting washer may be formed by a welding seam.

It is possible to introduce socket connectors 17 into the plastic material of housing jacket 6 in the region of the flange.

The detail view of FIG. 3 shows additional sensors, which are disposed on the outside of bottom 8. The ducts of the electric contacts in bottom 8 have a glass or ceramic insulation.

An additional example embodiment is represented in FIGS. 4 and 5. A metal housing body 19 is developed in the shape of a hat. Box 2 and also the elements disposed therein may be similar to those of the example embodiment of FIG. 1. Socket connectors 21 are situated in a flange edge 20 of the hat shape. They may be introduced into the deep-drawn housing body by a stamping process, for instance. A sealing ring 22 is situated on top of flanged ring 20.

Housing body 19 may be covered by a housing jacket (not shown) made of a plastic material. The plastic coat may be developed as very thin layer. In the region of sealing ring 22 the plastic jacket or housing jacket is interrupted.

A cover 23 made of sheet metal or plastic may be disposed on the outside of bottom 8 to protect the subassemblies or sensors 18. Cover 23 may be welded or locked into place.

FIGS. 6 and 7 show an example embodiment of a liquid sensor. Once again, the housing body has a box 2 including a flanged ring 3. A circumferential sealing ring 22 is disposed on flanged ring 3. Side wall 4 of box 2 has at least partially an exterior thread. Using the exterior thread, the liquid sensor is able to be fixed in place in a duct using a thread. In order to be able to apply a tool to the liquid sensor, a hexagonal or square plate 25 may be disposed at flanged edge 3. The outer dimensions of plate 25 preferably correspond to the sizes of wrenches,

What is claimed is:

1. A liquid sensor, comprising:
 a metal housing body, which has a box and a flanged ring circumferentially enclosing the box;
 a housing jacket made of plastic material, which is disposed on an outer side of the housing body; and
 a sealing ring, which is disposed circumferentially on the flanged ring and subdivides the housing jacket into two mutually insulated sections;
 wherein the box defines the interior space of the metal housing body and the flanged ring extends at an angle with respect to a wall of the box of the liquid sensor; and
 wherein a cylindrical capacitive sensor is welded to an exterior side of the box.

2. The liquid sensor according to claim 1, wherein the sealing ring contacts the metal housing body in a region of the flanged ring.

3. The liquid sensor according to claim 1, wherein an insert is inserted into the box, and electronic subassemblies for at least one of (a) controlling and (b) supplying the liquid sensor are disposed on top of the insert.

4. The liquid sensor according to claim 3, wherein the insert is sealingly welded to the box.

5. The liquid sensor according to claim 1, wherein a plug connection is fixed in place on the insert, and conductive spring elements are provided on the electronic subassemblies for electrical contacting of the plug connection.

6. The liquid sensor according to claim 1, wherein the box has an external thread on an outside for mounting the liquid sensor.

7. The liquid sensor according to claim 1, wherein socket connectors for mounting the liquid sensor are disposed in a first section of the two mutually insulated sections of the housing jacket.

8. The liquid sensor according to claim 1, wherein a second section of the two mutually insulated sections of the housing jacket covers at least side walls of the box.

9. The liquid sensor according to claim 1, wherein the liquid sensor is arranged as at least one of (a) a liquid-level sensor for fuel and (b) a sensor for an engine-oil composition.

* * * * *